United States Patent

Vanhoye et al.

Patent Number: 5,169,980
Date of Patent: Dec. 8, 1992

[54] NEW PROCESS FOR THE MANUFACTURE OF BENZYL METHACRYLATE AND ITS DERIVATIVES WHICH ARE HALOGENATED OR ALKYLATED ON THE AROMATIC NUCLEUS

[75] Inventors: Didier Vanhoye, Forbach; Paul Grosius, Petite-Rosselle; Patrice Hurtel, St. Avold, all of France

[73] Assignee: Elf Atochem S.A., Paris, France

[21] Appl. No.: 694,287

[22] Filed: May 3, 1991

[30] Foreign Application Priority Data

May 3, 1990 [FR] France ............................ 90 05580

[51] Int. Cl.$^5$ .............................................. C07C 69/52
[52] U.S. Cl. ....................................... 560/221; 560/55
[58] Field of Search ........................... 560/221, 55, 221

[56] References Cited

FOREIGN PATENT DOCUMENTS 42-14937 8/1967 Japan .

Primary Examiner—Paul J. Killos
Attorney, Agent, or Firm—Millen, White, Zelano and Branigan

[57] ABSTRACT

This process for the manufacture of benzyl methacrylate and of its halogenated or alkylated derviatives by the reaction of benzyl chloride or of one of its halogenated or alkylated derivatives with an alkali metal methacrylate is characterized in that the reaction is carried out in the presence of not more than 3 mol %, based on the benzyl chloride or a derivative, of a tertiary amine. The alkali metal is chosen especially from lithium, potassium and sodium. The tertiary amine is preferably a tertiary diamine of general formula:

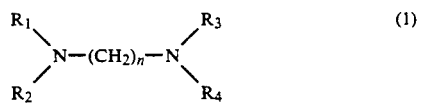

(1)

in which n is an integer ranging from 1 to 10 and $R_1$, $R_2$, $R_3$ and $R_4$, which are identical or different, are alkyl, cycloalkyl or aryl radicals containing from 1 to 12 carbon atoms, functionalized if appropriate and, if appropriate, such that they form a heterocyclic ring with the nitrogen atom(s) carrying them.

25 Claims, No Drawings

NEW PROCESS FOR THE MANUFACTURE OF BENZYL METHACRYLATE AND ITS DERIVATIVES WHICH ARE HALOGENATED OR ALKYLATED ON THE AROMATIC NUCLEUS

BACKGROUND OF THE INVENTION

The present invention relates to a new method of synthesis enabling benzyl methacrylate and some of its derivatives to be obtained in a simple manner and in a high yield.

Benzyl methacrylate and its derivatives which are chlorinated or alkylated on the aromatic nucleus are methacrylic monomers which are widely employed, for example, in copolymerization with other monomers, especially acrylic, methacrylic and vinylaromatic monomers and the resultant copolymers are fabricated into various conventional products described in the literature. It is therefore important from the viewpoint of uses in copolymerization that these monomers may be obtained in a manner which is as simple and as economical as possible.

One of the methods of synthesis of benzyl methacrylates and of its most commonly employed derivatives consists of the transesterification of methyl methacrylate with benzyl alcohol or its derivatives which are chlorinated or alkylated on the aromatic nucleus. However, this reaction is made tricky by the fact that benzyl alcohol can be easily oxidized to benzaldehyde by the atmospheric oxygen needed for stabilizing the monomer under the reaction conditions.

Another method of synthesis consists in starting with benzyl chloride. Thus, Soviet Patent No. 415,345 describes the synthesis of benzyl methacrylate from benzyl chloride and methacrylic acid in an aprotic polar solvent such as dimethylformamide and in the presence of a stoichiometric quantity of a scavenger for hydrochloric acid, such as a tertiary amine, at a temperature of 20° C. to 60° C. When this reaction is performed at 50° C. for 2.5 hours, the yield attained is 75%. Furthermore, J. Dvorak in Chem. Abstracts, 53, 2144b has described the synthesis of benzyl methacrylat from benzyl chloride and sodium methacrylate in the presence of a tertiary amine. When using 10 mol % of tributylamine, a 60% yield of benzyl methacrylate is thus obtained after 2.5 hours.

SUMMARY OF THE INVENTION

The problem which the present invention aims to solve consists in providing a simple and economical process for the synthesis of benzyl methacrylate and of its derivatives while avoiding the abovementioned disadvantages of the synthesis starting with benzyl alcohol, while greatly improving the yields of the known syntheses starting from benzyl chloride.

The present invention is based on the finding that the objectives can be attained by carrying out the reaction of benzyl chloride or of its halogenated or alkylated derivatives at a moderate temperature, in the presence of a truly catalytic proportion of a tertiary amine and preferably in the presence of a particular solvent such as acetonitrile or toluene.

Thus, the present invention provides a process for the manufacture of benzyl methacrylate or of its halogenated or alkylated derivatives by the reaction of benzyl chloride or of one of its halogenated or alkylated derivatives with an alkali methal methacrylate, characterized in that the said reaction is carried out in the presence of a catalytic quantity of not more than 3 mol %, based on the benzyl chloride or one of its derivatives, of a tertiary amine.

Benzyl methacrylate or its derivatives which are halogenated or alkylated on the aromatic nucleus can be denoted by the general formula:

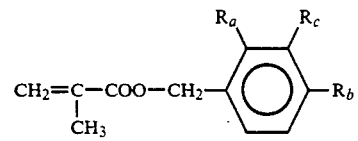

in which
$R_a$ = H or Cl,
$R_b$ = H, Cl, $CH_3$ or

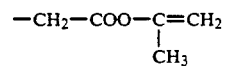

$R_c$ = H or $CH_2$=CH—

Benzyl chloride or its halogenated or alkylated derivatives employed as starting materials for implementing the process of the invention can be denoted by the general formula:

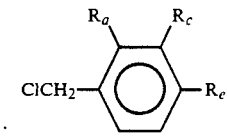

in which:
$R_a$ = H or Cl,
$R_b$ = H, Cl, $CH_3$ or $CH_2Cl$,
$R_c$ = H or $CH_2$=CH—

It has been found, in fact, that it is possible to manufacture benzyl methacrylate and its derivatives by using benzyl chloride and its corresponding derivatives such as 2-chlorobenzyl chloride, 2,4-dichlorobenzyl chloride, 4-methylbenzyl chloride, 4-chloromethylbenzyl chloride, 4-chlorobenzyl chloride, 3-vinylbenzyl chloride, etc.

The alkali metal methacrylate employed for the reaction according to the invention may be a lithium, potassium or sodium methacrylate. When potassium methacrylate is employed it can be prepared by saponification of methyl methacrylate or by neutralization of methacrylic acid with potassium carbonate, the latter being preferably in excess relative to the acid. In this case, it is possible not to isolate potassium methacrylate before its reaction with benzyl chloride or with one of its derivatives, and the process of manufacture according to the invention can therefore be considered similar to a process of synthesis in two stages from methacrylic acid.

The tertiary amine employed as catalyst in the process according to the invention is preferably a tertiary diamine, for example of the general formula:

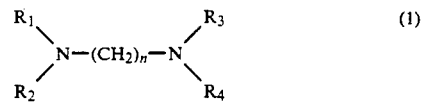

(1)

in which n is an integer ranging from 1 to 10, and $R_1$, $R_2$, $R_3$ and $R_4$, which are identical or different, are alkyl, cycloalkyl or aryl radicals containing from 1 to 12 carbon atoms, functionalized if appropriate and, if appropriate, such that they form a heterocyclic ring with the nitrogen atom(s) carrying them. Examples of tertiary diamines which can be employed include but are not limited to tetramethylethylenediamine and tetramethylpropyldiamine. The compound may also be a polyamine containing more than two tertiary amine functional groups.

The process of manufacture according to the invention is preferably implemented under the following conditions:

a molar ratio of alkali metal methacrylate/benzyl chloride or its derivatives of approximately between 0.9 and 1.5, preferably between 1.0 and 1.2;

a molar proportion of tertiary amine/benzyl chloride or its derivatives of approximately between 0.2% and 3%, preferably approximately between 0.5% and 2%.

The process of manufacture according to the invention is preferably carried out in the presence of a solvent of very high polarity, such as, for example, acetonitrile or toluene, which forms another solvent which can be employed. Other solvents which can also be employed are dimethylformamide, tetrahydrofuran, dimethyl sulfoxide, N-methylpyrrolidone, 1,2-dichloroethane, and the like. The solvent is preferably employed in a proportion of approximately from 0.3 to 10 volumes per 1 volume of benzyl chloride or of its derivatives.

The reaction temperature will quite obviously be chosen as a function of the boiling temperature of the solvent which is chosen. However, as a general rule, it is unnecessary to resort to high reaction temperatures, in view of the fact that more moderate temperatures suffice to ensure a high yield of benzyl methacrylate or of one of its derivatives, and suitable reaction velocities. The reaction temperature will therefore generally be chosen approximately between 20° C. and 140° C., preferably approximately between 30° C. and 110° C. By way of example, when acetonitrile is employed as solvent, the temperature is chosen approximately between 30° C. and 60° C.

The reaction of the process according to the invention is preferably carried out in the presence of at least one polymerization inhibitor, employed, for example, in a proportion of 0.05% to 0.5% by weight based on the weight of alkali metal methacrylate. Examples of polymerization inhibitors which can be employed and which may be mentioned are especially phenothiazine, hydroquinone methyl ether, N,N-diethylhydroxylamine, nitrobenzene, di-tert-butylcatechol, butylhydroxytoluene, hydroquinone, p-anilinophenol, di(2-ethylhexyl)octylphenyl phosphite, methylene blue and their mixtures in all proportions.

The process of manufacture according to the invention is preferably carried out under atmospheric pressure. However, use of super or subatmospheric pressures does not generally impair the performance of the present invention. The process can be carried out batchwise or continuously, use being made of the usual knowledge of a person skilled in the art. The reaction time is obviously a function of the other reaction parameters already referred to, especially the molar ratios of the reactants, the quantity of solvent and the reaction temperature. However, it is generally approximately between 1 and 10 hours. At the end of the actual reaction, the alkali metal chloride formed is separated off by filtration and is preferably washed with the same solvent as that employed for the reaction. The filtrate is then subjected to a solvent evaporation stage, for example at reduced pressure, in order to recover benzyl methacrylate or the corresponding derivative. These are generally obtained in a purity of at least 95%, with a very small residual quantity of the starting benzyl chloride or derivative. A product of very high purity—higher than 99%—which is suitable for the abovementioned applications can then be obtained by distillation at reduced pressure. The tertiary amine can be partly or completely recovered during the distillation or removed by washing the crude product with water before or after solvent removal. This latter treatment also makes it possible to remove the traces of salt which may be found to be detrimental during subsequent purification.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire disclosures of all applications, patents and publications, cited above and below, and of corresponding application France 90 05580, filed May 3, 1990, are hereby incorporated by reference.

EXAMPLES

Example 1

132 g of 85% potassium hydroxide (2 moles) are introduced cautiously into a 1-liter reactor fitted with a central mechanical stirrer and a 4-plate distillation column supporting a column head with a separator, containing 241 g of methanol (7.5 moles). The reaction is highly exothermic and cooling must be applied to maintain the temperatures at 60°-65° C. Stirring is continued for 20 minutes until everything has dissolved. 220 g of methyl methacrylate (2.2 moles) are introduced slowly into the stirred reactor, the temperature is kept at 60° C. for one hour, the mixture is cooled to room temperature and the unreacted potassium hydroxide is neutralized with methacrylic acid (color indicator employed: phenolphthalein). Potassium methacrylate crystals formed are separated off by filtration and are dried under vacuum at about 40°-60° C. by means of a rotary evaporator.

The following are introduced into a 250-ml reactor fitted with a central stirrer and a condenser:

68.2 g of the potassium methacrylate prepared in the preceding stage and not subjected to any further purification, 63.3 g of benzyl chloride, 0.59 g of tetramethylethylenediamine, 0.07 g of hydroquinone methyl ether, and 150 ml of acetonitrile.

The reaction mixture is then heated to a temperature of 60° C. while dry air is bubbled through for 6 hours. After being allowed to cool to room temperature, it is filtered through a porosity 2 glass sinter and the precipitate collected is washed with 50 ml of acetonitrile. The light-yellow filtrate is then stripped of solvent by means of a rotary evaporator operating at a temperature of 60° C. and at a pressure of 0.065 bar. The removal of the acetonitrile thus makes it possible to recover benzyl methacrylate in the yield Y (expressed in %) shown in the table below.

Example 2

The experimental procedure of Example 1 is reproduce with the exception of the reaction temperature, which is set at 30° C. instead of 60° C., and the quantity of tetramethylethylenediamine, which is doubled to 1.18 g. Under these conditions, benzyl methacrylate is formed in the yield Y shown in the table below.

Example 3

The experimental procedure of Example 1 is reproduced, with the double exception of:
the reaction temperature set at 50° C., and
the quantity of tetramethylethylenediamine, raised to 1.18 g.
The yield of the reaction carried out under these conditions is shown in the table below.

Example 4

The experimental procedure of Example 1 is reproduced with the exception of the quantity of tetramethylethylenediamine, lowered to 0.295 g. The yield of the reaction carried out under these conditions is shown in the table below.

Example 5

The experimental procedure of Example 1 is reproduced with the exception of the quantity of potassium methacrylate, which is lowered to 61.5 g. The yield of the reaction carried out in these conditions is shown in the table below.

Example 6

The experimental procedure of Example 1 is reproduced with the acetonitrile being replaced, as solvent, with an equal quantity of toluene and with the reaction temperature raised to 110° C. The yield of the reaction carried out under these conditions is shown in the table below.

TABLE

| Example | 1 | 2 | 3 | 4 | 5 | 6 |
|---|---|---|---|---|---|---|
| R | 92 | 85 | 91 | 86 | 88 | 83 |

Example 7

The following are introduced into a 2-liter reactor fitted with a central mechanical stirrer, a column head with a separator supporting a condenser and a dropping funnel:
279 cm$^3$ of a potassium hydroxide solution (10.5 moles/l concentration), that is a solution containing 2.95 moles of potassium hydroxide,
1300 grams of toluene,
0.925 grams of butylhydroxytoluene.
The reactor is then heated to a temperature of between 40°–43° C. and 250 grams of methacrylic acid are then introduced over 1 hour 30 minutes with the aid of a dropping funnel.
The reactor is then placed at a reduced pressure of 200 mbar and heated to 60° C.; the water formed is distilled off. The reaction mixture is cooled and is then filtered on a Buchner funnel. The potassium methacrylate crystals obtained are then dried under vacuum at 50° C. by means of a rotary evaporator. Potassium methacrylate is obtained in a purity of 95% (determined by NMR analysis).

The following are introduced into a 250-ml reactor fitted with a central stirrer and a condenser:
71.8 g of potassium methacrylate prepared in the previous stage,
80.5 g of 2-chlorobenzyl chloride,
0.845 grams of tetramethylpropyldiamine,
0.1 gram of butylhydroxytoluene,
110 grams of toluene.
The reactor is then immersed in an oil bath heated to 90° C. and is then left stirred for 6 hours and then returned to room temperature after 2 hours; the contents are then filtered through a glass sinter. The filtrate is then washed with 60 cm$^3$ of toluene. 0.158 grams of hydroxyquinone methyl ether are then added and the toluene is then removed with the aid of a rotary evaporator operating at a temperature of 60° C. at a pressure of 60 mm Hg and then at a pressure of 20 mm Hg.

2-Chlorobenzyl methacrylate is then recovered in a 99.8% yield.

Example 8

Example 7 is repeated using the following ingredients:
70 grams of potassium methacrylate,
97.9 grams of 2,4-dichlorobenzyl chloride,
0.754 grams of tetramethylethylenediamine,
0.1 gram of butylhydroxytoluene,
110 grams of toluene.
After treatment as in Example 7, 2,4-dichlorobenzyl methacrylate is obtained in a 97.6% yield.

Example 9

Example 7 is repeated with the aid of the following reactants:
70 grams of potassium methacrylate,
140.6 grams of 4-methylbenzyl chloride,
0.787 grams of tetramethylethylenediamine,
0.5 grams of butylhydroxytoluene,
110 grams of toluene.
4-Methylbenzyl methacrylate is obtained in a 97.4% yield.

Example 10

The procedure of Example 7 is reproduced using the following reactants:
70.3 grams of potassium methacrylate,
43.8 grams of 4-chloromethylbenzyl chloride,
0.824 grams of tetramethylethylenediamine,
0.10 gram of butylhydroxytoluene,
170 grams of toluene.
After reaction and treatment as in Example 1, benzyl dimethacrylate is obtained in a 68.6% yield.

Example 11

The experimental procedure of Example 7 is reproduced with the aid of the following reactants:
70.5 grams of potassium methacrylate,
81 grams of 4-chlorobenzyl chloride,
0.733 grams of tetramethylethylenediamine,
0.1 grams of butylhydroxytoluene,
110 grams of toluene.
At the end of reaction 4-chlorobenzyl methacrylate is obtained in a 98.2% yield.

Example 12

Example 7 is repeated using the following ingredients:
70 grams of potassium methacrylate,
109.9 grams of 3-vinylbenzyl chloride,
0.79 grams of tetramethylethylenediamine,
0.1 grams of butylhydroxytoluene,
110 grams of toluene.

After treatment as in Example 1, 3-vinylbenzyl methacrylate is collected.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. In a process for the manufacture of benzyl methacrylate or derivatives thereof the formula:

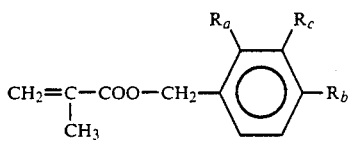

wherein:
$R_a$=H or Cl,
$R_b$=H, Cl, CH$_3$ or

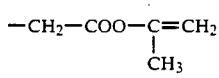

$R_c$=H or CH$_2$=CH— comprising reacting benzyl chloride or a corresponding derivative thereof which is halogenated or alkylated on the aromatic nucleus with an alkali methal methacrylate, the improvement which comprises conducting the reaction in the presence of a catalytic quantity of not more than 3 mol %, based on the benzyl chloride or corresponding derivative thereof, of a tertiary diamine of the formula:

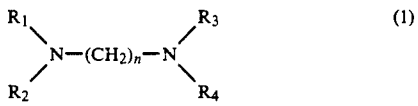

in which n is an integer ranging from 1 to 10, and $R_1$, $R_2$, $R_3$ and $R_4$, which are identical or different, are alkyl, cycloalkyl or aryl radicals containing from 1 to 12 carbon atoms.

2. A process of manufacture according to claim 1, characterized in that the alkali metal is lithium, potassium or sodium.

3. A process of manufacture according to claim 1, wherein the tertiary amine is tetramethylethylenediamine or tetramethylpropyldiamine.

4. A process of manufacture according to claim 1, wherein the molar ratio of alkali metal methacrylate/benzyl chloride or said derivative thereof is between 0.9 and 1.5.

5. A process of manufacture according to claim 1, wherein the molar proportion of tertiary amine/benzyl chloride derivative thereof is between 0.5 and 2%.

6. A process of manufacture according to claim 1, wherein the reaction is carried out in the presence of a polar solvent.

7. A process of manufacture according to claim 1, wherein the reaction is carried out in the presence of a solvent which is acetonitrile or toluene.

8. A process of manufacture according to claim 1, wherein the reaction is carried out at a temperature of between 20° C. and 140° C.

9. A process of manufacture according to claim 1, wherein the reaction is carried out for a period of between 1 and 10 hours.

10. A process of manufacture according to claim 2, wherein the tertiary amine is tetramethylethylenediamine or tetramethylpropyldiamine.

11. A process of manufacture according to claim 4, wherein the molar ratio of alkali metal methacrylate/benzyl chloride or said derivative thereof is between 0.9 and 1.5.

12. A process of manufacture according to claim 1, wherein the molar ratio of alkali metal methacrylate/benzyl chloride or said derivative thereof is between 0.9 and 1.5.

13. A process of manufacture according to claim 10, wherein the molar ratio of alkali metal methacrylate/benzyl chloride or said derivative thereof is between 0.9 and 1.5.

14. A process of manufacture according to claim 3, wherein the molar proportion of tertiary amine/benzyl chloride derivative thereof is between 0.5 and 2%.

15. A process of manufacture according to claim 13, wherein the molar proportion of tertiary amine/benzyl chloride derivative thereof is between 0.5 and 2%.

16. A process of manufacture according to claim 14, wherein the reaction is carried out in the presence of a solvent which is acetonitrile or toluene.

17. A process of manufacture according to claim 15, wherein the reaction is carried out in the presence of a solvent which is acetonitrile or toluene.

18. A process of manufacture according to claim 17, wherein the reaction is carried out for a period of between 1 and 10 hours.

19. A process according to claim 1, wherein the process is conducted in the presence of a polymerization inhibitor.

20. A process according to claim 18, wherein the process is conducted in the presence of a polymerization inhibitor.

21. A process according to claim 1, wherein the polymerization inhibitor is butylhydroxytoluene.

22. A process according to claim 20, wherein the polymerization inhibitor is butylhydroxytoluene.

23. A process according to claim 22, wherein the alkali metal methacrylate is potassium methacrylate.

24. A process according to claim 1, wherein the tertiary amine is tetramethylpropyldiamine.

25. A process according to claim 1, wherein the tertiary amine is tetramethylethylenediamine.

* * * * *